US012758706B2

(12) United States Patent
Mandro et al.

(10) Patent No.: US 12,758,706 B2
(45) **Date of Patent: *Oct. 13, 2026**

(54) OCCLUSION DETECTION SYSTEM AND METHOD

(71) Applicant: DEKA Products Limited Partnership, Manchester, NH (US)

(72) Inventors: Marc A. Mandro, Bow, NH (US); Robert J. Bryant, Manchester, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 55 days.

This patent is subject to a terminal disclaimer.

(21) Appl. No.: 18/913,123

(22) Filed: Oct. 11, 2024

(65) Prior Publication Data

US 2025/0032703 A1 Jan. 30, 2025

Related U.S. Application Data

(63) Continuation of application No. 18/300,502, filed on Apr. 14, 2023, now Pat. No. 12,115,344, which is a continuation of application No. 16/995,142, filed on Aug. 17, 2020, now Pat. No. 11,628,247, which is a continuation of application No. 16/414,940, filed on May 17, 2019, now Pat. No. 10,744,257, which is a continuation of application No. 15/851,906, filed on (Continued)

(51) Int. Cl.

| | |
|---|---|
| ***A61M 5/145*** | (2006.01) |
| ***A61M 5/168*** | (2006.01) |
| ***A61M 5/50*** | (2006.01) |

(52) U.S. Cl.

CPC ...... *A61M 5/1452* (2013.01); *A61M 5/14566* (2013.01); *A61M 5/5086* (2013.01); *A61M 2005/14573* (2013.01); *A61M 2005/16863* (2013.01); *A61M 2205/332* (2013.01); *A61M 2205/52* (2013.01); *A61M 2205/8206* (2013.01)

(58) Field of Classification Search

CPC ............ A61M 5/1452; A61M 5/14566; A61M 5/5086; A61M 2005/14573; A61M 2005/16863; A61M 2205/332; A61M 2205/52; A61M 2205/8206

See application file for complete search history.

(56) References Cited

U.S. PATENT DOCUMENTS 5,712,795 A * 1/1998 Layman ................ A61M 5/142
324/426
2007/0149926 A1 * 6/2007 Moberg .............. A61M 5/1456
604/152

(Continued)

*Primary Examiner* — Sisay Yacob

(74) *Attorney, Agent, or Firm* — McCormick, Paulding & Huber PLLC

(57) ABSTRACT

A method, computer program product, and infusion pump assembly for determining a first rate-of-change force reading that corresponds to the delivery of a first dose of an infusible fluid via an infusion pump assembly. At least a second rate-of-change force reading is determined that corresponds to the delivery of at least a second dose of the infusible fluid via the infusion pump assembly. An average rate-of-change force reading is determined based, at least in part upon the first rate-of-change force reading and the at least a second rate-of-change force reading.

15 Claims, 2 Drawing Sheets

Related U.S. Application Data

Dec. 22, 2017, now Pat. No. 10,314,969, which is a continuation of application No. 14/703,473, filed on May 4, 2015, now Pat. No. 9,849,235, which is a continuation of application No. 13/549,962, filed on Jul. 16, 2012, now Pat. No. 9,024,768, which is a continuation of application No. 12/249,621, filed on Oct. 10, 2008, now Pat. No. 8,223,028.

(56) References Cited

U.S. PATENT DOCUMENTS

| | | | | |
|---|---|---|---|---|
| 2007/0191770 | A1* | 8/2007 | Moberg ............ | A61M 5/14244<br>604/131 |
| 2008/0294108 | A1* | 11/2008 | Briones ............ | A61M 5/14244<br>604/131 |
| 2009/0076461 | A1* | 3/2009 | Susi ...................... | A61M 5/172<br>604/246 |
| 2010/0080720 | A1 | 4/2010 | Miyazaki et al. | |

* cited by examiner

| Title | Initial | Final | Rate-of-Change |
| --- | --- | --- | --- |
| FR01 | 0.00 lbs. | 0.00 lbs. | 0.00 lbs. |
| FR02 | 0.00 lbs. | 0.00 lbs. | 0.00 lbs. |
| FR03 | 0.00 lbs. | 0.00 lbs. | 0.00 lbs. |
| FR04 | 0.00 lbs. | 0.00 lbs. | 0.00 lbs. |
| FR05 | 0.00 lbs. | 0.00 lbs. | 0.00 lbs. |
| FR06 | 0.00 lbs. | 0.00 lbs. | 0.00 lbs. |
| FR07 | 0.00 lbs. | 0.00 lbs. | 0.00 lbs. |
| FR08 | 0.00 lbs. | 0.00 lbs. | 0.00 lbs. |
| FR09 | 0.00 lbs. | 0.00 lbs. | 0.00 lbs. |
| FR10 | 0.00 lbs. | 0.00 lbs. | 0.00 lbs. |

| | | | |
| --- | --- | --- | --- |
| FR31 | 0.00 lbs. | 0.00 lbs. | 0.00 lbs. |
| FR32 | 0.00 lbs. | 0.00 lbs. | 0.00 lbs. |
| FR33 | 0.00 lbs. | 0.00 lbs. | 0.00 lbs. |
| FR34 | 0.00 lbs. | 0.50 lbs. | 0.50 lbs. |
| FR35 | 0.50 lbs. | 1.05 lbs. | 0.55 lbs. |
| FR36 | 1.05 lbs. | 1.80 lbs. | 0.75 lbs. |
| FR37 | 1.80 lbs. | 2.30 lbs. | 0.50 lbs. |
| FR38 | 2.30 lbs. | 3.10 lbs. | 0.80 lbs. |
| FR39 | 3.10 lbs. | 3.80 lbs. | 0.70 lbs. |
| FR40 | 3.80 lbs. | 4.20 lbs. | 0.40 lbs. |
| AFR | --- | --- | 0.105 lbs. |

OCCLUSION DETECTION SYSTEM AND METHOD

CROSS REFERENCE TO RELATED APPLICATIONS

This application is a continuation of U.S. patent application Ser. No. 18/300,502, filed Apr. 14, 2023, which is a continuation of U.S. patent application Ser. No. 16/995,142, filed Aug. 17, 2020, which is a continuation of U.S. patent application Ser. No. 16/414,940, filed May 17, 2019, which is a continuation of U.S. patent application Ser. No. 15/851,906, filed Dec. 22, 2017, which is a continuation of U.S. patent application Ser. No. 14/703,473, filed May 4, 2015, which is a continuation of U.S. patent application Ser. No. 13/549,962, filed on Jul. 16, 2012, now U.S. Pat. No. 9,024,768, which is a continuation of U.S. patent application Ser. No. 12/249,621, filed Oct. 10, 2008, now U.S. Pat. No. 8,223,028, each of which is hereby incorporated herein by reference in its entirety.

TECHNICAL FIELD

This disclosure relates to occlusion detection and, more particularly, to occlusion detection within infusion pump assemblies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

Unfortunately, occlusions may occur that may impede/prevent the delivery of the infusible fluid, which may result in medical complications for the user.

SUMMARY OF DISCLOSURE

In a first implementation, a method includes determining a first rate-of-change force reading that corresponds to the delivery of a first dose of an infusible fluid via an infusion pump assembly. At least a second rate-of-change force reading is determined that corresponds to the delivery of at least a second dose of the infusible fluid via the infusion pump assembly. An average rate-of-change force reading is determined based, at least in part, upon the first rate-of-change force reading and the at least a second rate-of-change force reading.

One or more of the following features may be included. The average rate-of-change force reading may be compared to a threshold rate-of-change force reading to determine if the average rate-of-change force reading exceeds the threshold rate-of-change force reading. If the average rate-of-change force reading exceeds the threshold rate-of-change force reading, an alarm sequence may be initiated on the infusion pump assembly.

Determining the first rate-of-change force reading may include determining a first initial force reading prior to dispensing the first dose of the infusible fluid. The first dose of the infusible fluid may be dispensed. A first final force reading may be determined subsequent to dispensing the first dose of the infusible fluid. The first rate-of-change force reading may be determined based, at least in part, upon the first initial force reading and the first final force reading.

One or more of the first initial force reading and the first final force reading may be compared to a threshold force reading to determine if one or more of the first initial force reading and the first final force reading exceeds the threshold force reading. If one or more of the first initial force reading and the first final force reading exceeds the threshold force reading, an alarm sequence may be initiated on the infusion pump assembly.

Determining the at least a second rate-of-change force reading may include determining at least a second initial force reading prior to dispensing the at least a second dose of the infusible fluid. The at least a second dose of the infusible fluid may be dispensed. At least a second final force reading may be determined subsequent to dispensing the at least a second dose of the infusible fluid. The at least a second rate-of-change force reading may be determined based, at least in part, upon the at least a second initial force reading and the at least a second final force reading.

The infusion pump assembly may include a battery assembly configured to power the infusion pump assembly. An actual voltage level of the battery assembly may be compared to a minimum voltage requirement to determine if the actual voltage level meets the minimum voltage requirement. If the actual voltage level does not meet the minimum voltage requirement, an alarm sequence may be initiated on the infusion pump assembly.

One or more displaceable mechanical components included within the infusion pump assembly may be monitored to determine if the one or more displaceable mechanical components were displaced an expected displacement in response to delivery of one or more of the first dose of the infusible fluid and the second dose of the infusible fluid. If the one or more displaceable mechanical components were not displaced the expected displacement in response to delivery of one or more of the first dose of the infusible fluid and the second dose of the infusible fluid, an alarm sequence may be initiated on the infusion pump assembly.

In another implementation, a computer program product resides on a computer readable medium that has a plurality of instructions stored on it. When executed by a processor, the instructions cause the processor to perform operations including determining a first rate-of-change force reading that corresponds to the delivery of a first dose of an infusible fluid via an infusion pump assembly. At least a second rate-of-change force reading is determined that corresponds to the delivery of at least a second dose of the infusible fluid via the infusion pump assembly. An average rate-of-change force reading is determined based, at least in part, upon the first rate-of-change force reading and the at least a second rate-of-change force reading.

One or more of the following features may be included. The average rate-of-change force reading may be compared to a threshold rate-of-change force reading to determine if the average rate-of-change force reading exceeds the threshold rate-of-change force reading. If the average rate-of-change force reading exceeds the threshold rate-of-change force reading, an alarm sequence may be initiated on the infusion pump assembly.

Determining the first rate-of-change force reading may include determining a first initial force reading prior to dispensing the first dose of the infusible fluid. The first dose of the infusible fluid may be dispensed. A first final force reading may be determined subsequent to dispensing the first dose of the infusible fluid. The first rate-of-change force reading may be determined based, at least in part, upon the first initial force reading and the first final force reading.

One or more of the first initial force reading and the first final force reading may be compared to a threshold force reading to determine if one or more of the first initial force reading and the first final force reading exceeds the threshold force reading. If one or more of the first initial force reading and the first final force reading exceeds the threshold force reading, an alarm sequence may be initiated on the infusion pump assembly.

Determining the at least a second rate-of-change force reading may include determining at least a second initial force reading prior to dispensing the at least a second dose of the infusible fluid. The at least a second dose of the infusible fluid may be dispensed. At least a second final force reading may be determined subsequent to dispensing the at least a second dose of the infusible fluid. The at least a second rate-of-change force reading may be determined based, at least in part, upon the at least a second initial force reading and the at least a second final force reading.

The infusion pump assembly may include a battery assembly configured to power the infusion pump assembly. An actual voltage level of the battery assembly may be compared to a minimum voltage requirement to determine if the actual voltage level meets the minimum voltage requirement. If the actual voltage level does not meet the minimum voltage requirement, an alarm sequence may be initiated on the infusion pump assembly.

One or more displaceable mechanical components included within the infusion pump assembly may be monitored to determine if the one or more displaceable mechanical components were displaced an expected displacement in response to delivery of one or more of the first dose of the infusible fluid and the second dose of the infusible fluid. If the one or more displaceable mechanical components were not displaced the expected displacement in response to delivery of one or more of the first dose of the infusible fluid and the second dose of the infusible fluid, an alarm sequence may be initiated on the infusion pump assembly.

In another implementation, an infusion pump assembly is configured to perform operations including determining a first rate-of-change force reading that corresponds to the delivery of a first dose of an infusible fluid via an infusion pump assembly. At least a second rate-of-change force reading is determined that corresponds to the delivery of at least a second dose of the infusible fluid via the infusion pump assembly. An average rate-of-change force reading is determined based, at least in part, upon the first rate-of-change force reading and the at least a second rate-of-change force reading.

One or more of the following features may be included. The average rate-of-change force reading may be compared to a threshold rate-of-change force reading to determine if the average rate-of-change force reading exceeds the threshold rate-of-change force reading. If the average rate-of-change force reading exceeds the threshold rate-of-change force reading, an alarm sequence may be initiated on the infusion pump assembly.

Determining the first rate-of-change force reading may include determining a first initial force reading prior to dispensing the first dose of the infusible fluid. The first dose of the infusible fluid may be dispensed. A first final force reading may be determined subsequent to dispensing the first dose of the infusible fluid. The first rate-of-change force reading may be determined based, at least in part, upon the first initial force reading and the first final force reading.

One or more of the first initial force reading and the first final force reading may be compared to a threshold force reading to determine if one or more of the first initial force reading and the first final force reading exceeds the threshold force reading. If one or more of the first initial force reading and the first final force reading exceeds the threshold force reading, an alarm sequence may be initiated on the infusion pump assembly.

Determining the at least a second rate-of-change force reading may include determining at least a second initial force reading prior to dispensing the at least a second dose of the infusible fluid. The at least a second dose of the infusible fluid may be dispensed. At least a second final force reading may be determined subsequent to dispensing the at least a second dose of the infusible fluid. The at least a second rate-of-change force reading may be determined based, at least in part, upon the at least a second initial force reading and the at least a second final force reading.

The infusion pump assembly may include a battery assembly configured to power the infusion pump assembly. An actual voltage level of the battery assembly may be compared to a minimum voltage requirement to determine if the actual voltage level meets the minimum voltage requirement. If the actual voltage level does not meet the minimum voltage requirement, an alarm sequence may be initiated on the infusion pump assembly.

One or more displaceable mechanical components included within the infusion pump assembly may be monitored to determine if the one or more displaceable mechanical components were displaced an expected displacement in response to delivery of one or more of the first dose of the infusible fluid and the second dose of the infusible fluid. If the one or more displaceable mechanical components were not displaced the expected displacement in response to delivery of one or more of the first dose of the infusible fluid and the second dose of the infusible fluid, an alarm sequence may be initiated on the infusion pump assembly.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
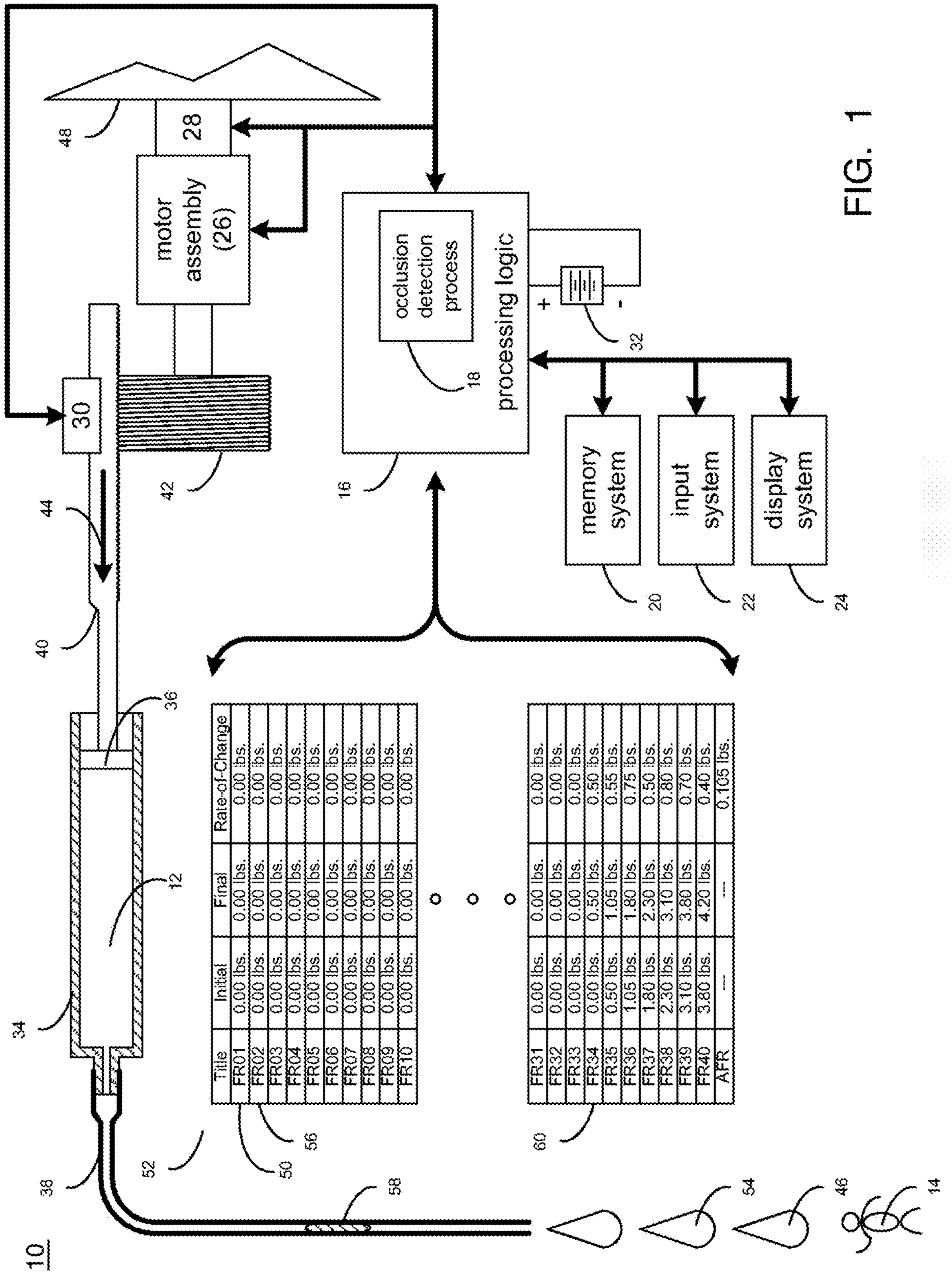
FIG. 1 is a diagrammatic view of an infusion pump assembly executing an occlusion detection process.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs.

Infusion pump assembly 10 may include processing logic 16 that executes one or more processes that may be required for infusion pump assembly 10 to operate properly. An example of such a process may include but is not limited to occlusion detection process 18, which will be discussed below in greater detail. Processing logic 16 may include one or more microprocessors (not shown), one or more input/output controllers (not shown), and cache memory devices (not shown). One or more data buses and/or memory buses may be used to interconnect processing logic 16 with one or more subsystems.

Examples of such subsystems may include but are not limited to memory system 20, input system 22, display system 24, motor assembly 26, force sensor 28, and displacement detection device 30. Infusion pump assembly 10 may include a power source (e.g. battery assembly 32) for providing electrical power to processing logic 16 and one or more of the subsystems (e.g., memory system 20, input system 22, display system 24, motor assembly 26, force sensor 28, and displacement detection device 30).

The instruction sets and subroutines of occlusion detection process 18, which may be stored on a storage device (e.g., memory system 20) accessible by processing logic 16, may be executed by one or more processors (not shown) and one or more memory architectures (e.g., memory system 20) included within infusion pump assembly 10. Examples of memory system 20 may include but are not limited to: a random access memory; a read-only memory; and a flash memory.

Infusion pump assembly 10 may include reservoir assembly 34 configured to contain infusible fluid 12. In some embodiments, the reservoir assembly 34 may be a reservoir assembly similar to that described in U.S. Patent Application Publication No. US-2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include, but is not limited to: a barrel with a plunger, a cassette or a container at least partially constructed of a flexible membrane.

Plunger assembly 36 may be configured to displace infusible fluid 12 from reservoir assembly 34 through cannula assembly 38 so that infusible fluid 12 may be delivered to user 14. In this particular embodiment, plunger assembly 36 is shown to be displaceable by partial nut assembly 40, which may engage lead screw assembly 42 that may be rotatable by motor assembly 26 in response to signals received from processing logic 16. In this particular embodiment, the combination of motor assembly 26, plunger assembly 36, partial nut assembly 40, and lead screw assembly 42 may form a pump assembly that effectuates the dispensing of infusible fluid 12 contained within reservoir assembly 34. An example of partial nut assembly 40 may include but is not limited to a nut assembly that is configured to wrap around lead screw assembly 42 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 10, infusible fluid 12 may be delivered to user 14 in accordance with e.g. a defined delivery schedule. For illustrative purposes only, assume that infusion pump assembly 10 is configured to provide 0.10 mL of infusible fluid 12 to user 14 every three minutes. Accordingly, every three minutes, processing logic 16 may provide the appropriate drive signals to motor assembly 26 to allow motor assembly 26 to rotate lead screw assembly 42 the appropriate amount so that partial nut assembly 40 (and therefore plunger assembly 36) may be displaced the appropriate amount in the direction of arrow 44 so that 0.10 mL of infusible fluid 12 are provided to user 14 (via cannula 38).

As discussed above, processing logic 16 may execute occlusion detection process 18, and occlusion detection process 18 may be configured to monitor one or more events that are occurring within infusion pump assembly 10 to determine whether or not an occlusion (e.g., a blockage) has occurred within e.g. cannula assembly 38.

Figure 2:
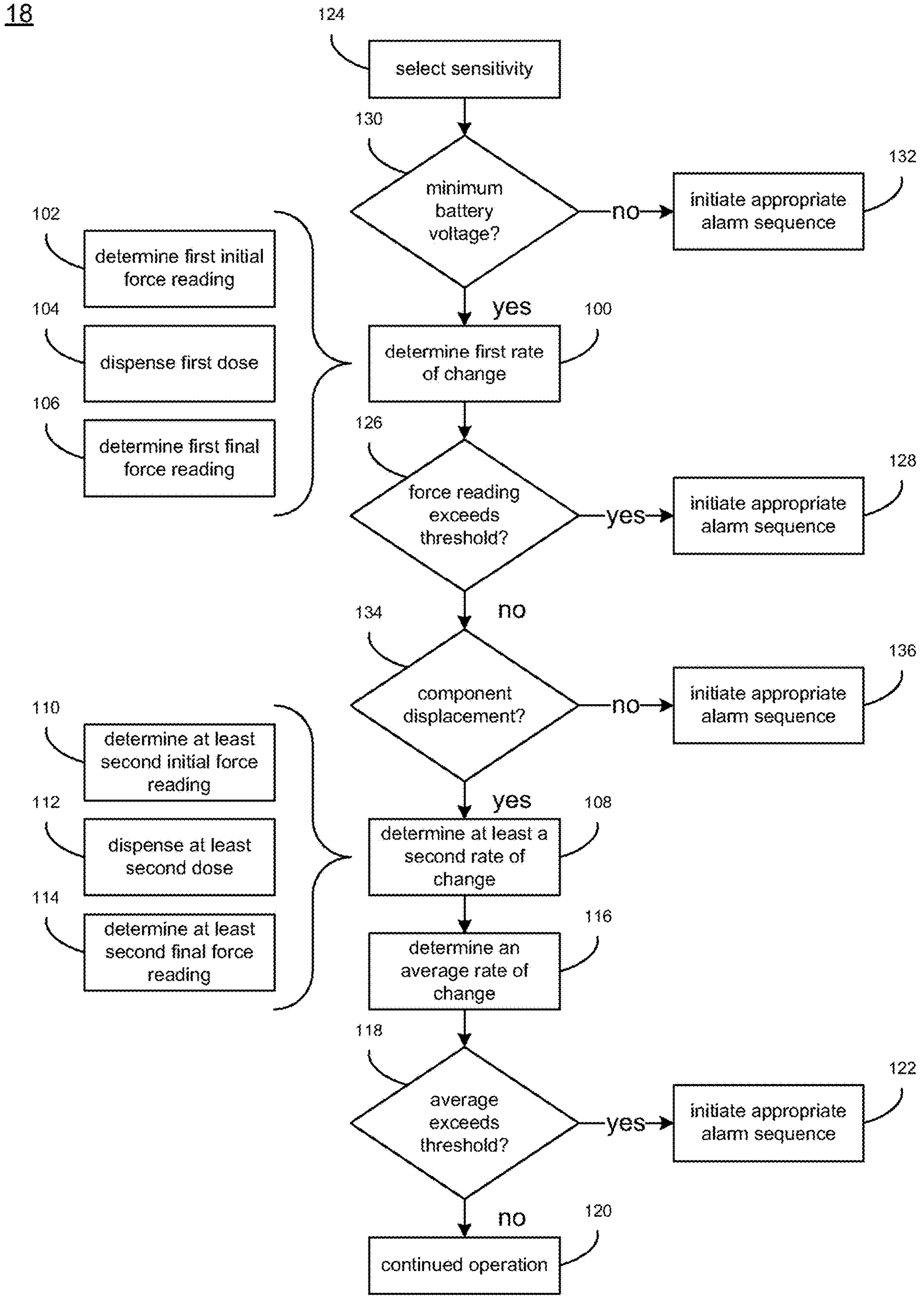
FIG. 2 is a flowchart of the occlusion detection process of FIG. 1.

Referring also to FIG. 2, occlusion detection process 18 may determine 100 a rate-of-change force reading (e.g., FR01) that corresponds to the delivery of first dose 46 of infusible fluid 12.

When determining 100 the rate-of-change force reading (e.g., FR01), occlusion detection process 18 may determine 102 an initial force reading prior to dispensing first dose 46 of infusible fluid 12. As discussed above, infusion pump assembly 10 may regularly dispense individual doses of infusible fluid 12 based upon one or more infusion schedules. For example and as discussed above, infusion pump assembly 10 may be configured to dispense 0.10 mL of infusible fluid 12 to user 14 every three minutes.

When determining 102 the initial force reading prior to dispensing first dose 46 of infusible fluid 12, occlusion detection process 18 may obtain the initial force reading from force sensor 28. Force sensor 28 may include one or more strain gauges and/or pressure sensing gauges and may be positioned between motor assembly 26 and an immovable object (e.g. bracket assembly 48) included within infusion pump assembly 10.

In one embodiment, force sensor 28 includes four strain gauges (not shown), such that: two of the four strain gauges are configured to be compressed when driving plunger 36 into reservoir assembly 34; and two of the four strain gauges are configured to be stretched when driving plunger 36 into reservoir assembly 34. The four strain gauges (not shown) may be connected to a Wheatstone Bridge (not shown) that produces an analog force signal (not shown) that is a function of the pressure sensed by force sensor 28. The analog force signal (not shown) produced by force sensor 28 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 28 to a level sufficient to be processed by the above-described analog-to-digital converter.

Provided that there is not an occlusion within e.g. cannula assembly 38, the initial force reading obtained by occlusion detection process 18 prior to infusion pump assembly 10 dispensing first dose 46 of infusible fluid 12 should be zero pounds. Once occlusion detection process 18 determines 102 the initial force reading, infusion pump assembly 10 may dispense 104 first dose 46 of infusible fluid 12 to user 14 via cannula assembly 38. While the system may be described above and/or below as having a force reading of zero pounds prior to and/or subsequent to dispensing infusible fluid 12, this is for illustrative purposes only, as frictional forces and/or backpressure may result in force readings that are slightly higher than zero pounds.

Once infusion pump assembly 10 dispenses 104 first dose 46 of infusible fluid 12 to user 14, occlusion detection process 18 may determine 106 a final force reading subsequent to dispensing 104 first dose 46 of infusible fluid 12. For example, once infusion pump assembly 10 has completely dispensed 104 first dose 46 of infusible fluid 12 to user 14, occlusion detection process 18 may obtain the final force reading from force sensor 28 in a process similar to that used to obtain the initial force reading from force sensor 28.

Occlusion detection process 18 may determine 100 the rate-of-change force reading (e.g., FR01) based, at least in part, upon the initial force reading and the final force reading. For example, occlusion detection process 18 may subtract the initial force reading from the final force reading to determine the net force change that occurred while dispensing (in this particular example) 0.10 mL of infusible fluid 12. As discussed above, provided that there are no occlusions within e.g. cannula assembly 38, the initial force reading (obtained from force sensor 28) should be zero and the final force reading (also obtained from force sensor 28) should also be zero. Accordingly, the rate-of-change force reading (e.g., FR01) determined 100 by occlusion detection process 18 should also be zero.

While the system is described above as determining 106 a final force reading subsequent to dispensing 104 first dose 46 of infusible fluid 12, this final force reading may actually be based upon the initial force reading that is taken for the next dose of infusible fluid 12. Accordingly, by allowing the initial force reading of the second dose of infusible fluid 12 to provide the data for the final force reading of the first dose of infusible fluid 12, the total number of force readings made may be reduced by 50%.

Once the rate-of-change force reading (e.g., FR01) is determined, occlusion detection process 18 may store the rate-of-change force reading (e.g., FR01) within e.g., storage cell 50 of storage array 52. Storage array 52 may be configured as a FIFO (first in, first out) buffer. Storage array 50 may be configured to allow occlusion detection process 18 to maintain a plurality of historical values for the rate-of-change force readings (e.g., FR01) discussed above. A typical embodiment of storage array 50 may include twenty or forty individual storage cells. As will be discussed below in greater detail, occlusion detection process 18 may process these historical values of the rate-of-change force readings to determine an average rate-of-change force reading over a desired infusible fluid volume/number of infusion cycles. While storage array 52 is illustrated in FIG. 1 as being a multi-column storage array, this is for illustrative purposes only and is not intended to be a limitation of this disclosure. For example, storage array 52 may be a single column storage array in which only the rate-of-change force readings are stored.

Motor assembly 26 may be configured as e.g., a brush-type DC electric motor. Further, motor assembly 26 may include a reduction gear assembly (not shown) that e.g. requires motor assembly 26 to rotate e.g., three-thousand revolutions for each revolution of lead screw assembly 42, thus increasing the torque and resolution of motor assembly 26 by a factor of three-thousand.

As discussed above, occlusion detection process 18 may process the historical values of the rate-of-change force readings to determine an average rate-of-change force reading over a desired infusible fluid volume/number of infusion cycles. For example, occlusion detection process 18 may determine an average rate-of-change force reading over each forty infusion cycles. Accordingly, occlusion detection process 18 may determine 108 additional rate-of-change force readings, each of which corresponds to the delivery of additional doses of infusible fluid 12. For example and for illustrative purposes only, occlusion detection process 18 may determine 108 thirty-nine additional rate-of-change force readings for the next thirty-nine infusion cycles. Each of these thirty-nine rate-of-change force readings may be stored in a unique storage cell of storage array 52. Once storage array 52 is completely full (i.e. contains forty rate-of-change force readings), occlusion detection process 18 may determine an average rate-of-change force reading for the set of forty rate-of-change force readings. Once this average rate-of-change force reading is determined, storage cell 52 may be cleared and the process of gathering additional rate-of-change force readings may be repeated.

When determining additional rate-of-change force readings, occlusion detection process 18 may determine 110 an initial force reading prior to dispensing the additional dose (e.g., dose 54) of infusible fluid 12. Dose 54 of infusible fluid may then be dispensed 112 by infusion pump assembly 10. Occlusion detection process 18 may determine 114 a final force reading subsequent to dispensing dose 54 of infusible fluid 12.

Occlusion detection process 18 may determine 108 the additional rate-of-change force readings (e.g., FR2) based, at least in part, upon the initial force reading and the final force reading for each additional dose of infusible fluid 12. As discussed above, provided that there are no occlusions within e.g. cannula assembly 38, the initial force reading (obtained from force sensor 28) should be zero and the final force reading (also obtained from force sensor 28) should also be zero. Accordingly, the rate-of-change force reading (e.g., FR2) determined 108 by occlusion detection process 18 should also be zero. As discussed above, once the additional rate-of-change force readings (e.g., FR2) are determined, occlusion detection process 18 may store the rate-of-change force reading (e.g., FR2) within e.g., storage cell 56 of storage array 52.

Assume for illustrative purposes that occlusion detection process 18 continues to calculate the rate-of-change force readings in the manner described above and continues to store these calculated rate-of-change force readings within storage array 52. Further, assume for illustrative purposes that infusion pump assembly 10 continues to operate properly (i.e. without any occlusions) for the first thirty-three infusion cycles. Accordingly, the first thirty-three rate-of-change force readings (FR01-FR33) are all zero, as their respective initial force reading and final force reading were all zero. However, assume for illustrative purposes that an occlusion (e.g. occlusion 58) occurs within cannula assembly 38 prior to calculating the thirty-fourth, rate-of-change force reading (e.g., FR34), which is stored within storage cell 60. Assume for illustrative purposes that when determining the thirty-fourth rate-of-change force reading (e.g., FR34), occlusion detection process 18 determines 110 an initial force reading of 0.00 pounds. When infusion pump assembly 10 begins to dispense 112 the thirty-fourth dose of infusible fluid 12, as occlusion 58 is present within cannula assembly 38, the fluid displaced from reservoir assembly 34 by plunger assembly 36 will not be able to pass through cannula assembly 38. Accordingly, the pressure within reservoir assembly 34 will begin to build. Therefore, assume for illustrative purposes that occlusion detection process 18 determines 114 a final force reading of 0.50 pounds. Accordingly, occlusion detection process 18 may determine 108 the rate-of-change force reading (e.g., FR34) to be 0.50 pounds minus 0.00 pounds, for a rate-of-change of 0.50 pounds.

Due to the presence of occlusion 58 within cannula assembly 38, when motor assembly 26 attempts to dispense the next dose of infusible fluid 12, 0.50 pounds of pressure sensed by force sensor 28 will still be present within fluid reservoir 34. Accordingly, when determining the thirty-fifth rate-of-change force reading (e.g., FR35), the initial force reading determined 110 by occlusion detection process 18 may be the same as the final force reading determined by occlusion detection process 18 when determining the thirty-fourth rate-of-change force reading (e.g., FR34).

Occlusion detection process 18 may determine 116 an average rate-of-change force reading (e.g., AFR) based, at least in part, upon all or a portion of the rate-of-change force readings included within storage array 52. Assume for illustrative purposes that occlusion detection process 18 is configured to consider all rate-of-change force readings (e.g., FR01-FR40) included within storage array 52. Accordingly, occlusion detection process 18 may calculate the mathematical average of all rate-of-change force readings (e.g., FR01-FR40) included within storage array 52. In this particular example, average rate-of-change force reading (e.g., AFR) has a mathematical value of 0.105 pounds. While the system is described above as being capable of considering all rate-of-change force readings (e.g., FR01-FR40) included within storage array 52, this is for illustrative purposes only and is not intended to be a limitation of this disclosure, as other configurations are possible. For example, occlusion detection process 18 may be configured to determine 116 an average rate-of-change force reading (e.g., AFR) once storage array 52 is populated with e.g., the first five rate-of-change force readings. If determining 116 an average rate-of-change force reading (e.g., AFR) prior to storage array 52 being completely populated, any unpopulated rows within storage array 52 may be populated with zeros.

Occlusion detection process 18 may compare 118 the average rate-of-change force reading (e.g., AFR) to a threshold rate-of-change force reading to determine if the average rate-of-change force reading (e.g., AFR) exceeds the threshold rate-of-change force reading. If the average rate-of-change force reading does not exceed the threshold rate-of-change force reading, infusion pump assembly 10 may continue 120 to operate normally. However, if the average rate-of-change force reading exceeds the threshold rate-of-change force reading, an alarm sequence may be initiated 122 on infusion pump assembly 10. For example, assuming for illustrative purposes that occlusion detection process 18 is configured to have a threshold rate-of-change force reading of 0.90 pounds, only after the average rate-of-change force reading (e.g., AFR) exceeds 0.90 pounds will the alarm sequence be initiated 120. Thus, in these embodiments, measuring the rate-of-change may ensure alarm sequences are triggered more reliably when actual occlusions have occurred. As described below, user 14, in some embodiments, may define the sensitivity of the system.

The sensitivity of occlusion detection process 18 may be based upon a user-defined sensitivity setting selected 124 by e.g., user 14. For example, assume that occlusion detection process 18 has two sensitivity settings, namely a high sensitivity setting and a low sensitivity setting. Further, assume that each of the sensitivity settings is associated with a unique manner of determining the rate-of-change force readings included within storage array 52. As discussed above, occlusion detection process 18 is described above as determining 100 a rate-of-change force reading (e.g., FR01) that corresponds to the delivery of first dose 46 of infusible fluid 12. Assume that when configured in the high sensitivity setting, occlusion detection process 18 may determine 100 a rate-of-change force reading that corresponds to the delivery of a comparatively smaller quantity of infusible fluid 12. Further, assume that when configured in the low sensitivity setting, occlusion detection process 18 may determine 100 a rate-of-change force reading that corresponds to the delivery of a comparatively larger quantity of infusible fluid 12. For example, assume that when in the high sensitivity setting, occlusion detection process 18 determines 100 a rate-of-change force reading that corresponds to the delivery of 0.10 mL of infusible fluid 12. Further, assume that when in the low sensitivity setting, occlusion detection process 18 determines 100 a rate-of-change force reading that corresponds to the delivery of a 0.20 mL dose 46 of infusible fluid 12. Accordingly, when placed in the high sensitivity setting, additional measurements are taken and occlusion detection process 18 is more responsive. However, false alarms may occur more frequently. Conversely, when placed in the low sensitivity setting, fewer measurements are taken and occlusion detection process 18 is less responsive. However, false alarms may occur less frequently due to the "averaging" effect of taking fewer measurements. Accordingly, in order to avoid nuisance alarms (or to reduce the number of alarms), the user (e.g. user 14) may select 124 the low sensitivity setting.

The alarm sequence initiated 122 may include any combination of visual-based (via display system 24), audible-based (via a speaker assembly, not shown), and vibration-based alarms (via a vibration assembly, not shown). User 14 may be able to select between the high-sensitivity setting and the low-sensitivity setting via one or more of input system 22 and display system 24.

While infusion pump assembly 10 is described above as delivering a plurality of identically-sized doses of infusible fluid 12 and calculating a rate-of-change force reading (e.g., FR01) for each dose of infusible fluid 12, this is for illustrative purposes only and is not intended to be a limitation of this disclosure. Specifically, infusion pump assembly 10 may be configured to provide non-identical doses of infusible fluid 12. Further, infusion pump assembly 10 may be configured to allow user 14 to manually administer a "bolus" dose of infusible fluid 12 in a size determined by user 14. Accordingly, occlusion detection system 18 may be configured to monitor the volume of infusible fluid 12 dispensed in each dose and may be configured to populate storage array 52 so that each rate-of-change force reading (e.g., FR01) included within storage array 52 is indicative of the rate-of-change force sensed by occlusion detection process 18 when dispensing an equivalent quantity of infusible fluid 12. Accordingly, occlusion detection system 18 may be configured to "normalize" the rate-of-change force readings determined based upon the quantity of infusible fluid delivered.

For example, assume that occlusion detection system 18 is configured so that a storage cell included within storage array 52 is populated each time 0.10 mL of infusible fluid 12 is dispensed. Assume for illustrative purposes only that user 14 decides to dispense a 0.25 mL dose of infusible fluid 12. As the 0.25 mL dose of infusible fluid 12 is greater than the 0.10 mL increments at which occlusion detection process 18 is configured to populate storage array 52, occlusion detection process 18 may record multiple entries (and, therefore, populate multiple storage cells) within storage array 52 for the single 0.25 mL dose of infusible fluid 12.

Specifically, assume that the initial force reading determined 110 prior to delivering the 0.25 mL dose of infusible fluid 12 is 0.00 pounds and the final force reading determined 114 after dispensing 112 the 0.25 mL dose of infusible fluid 12 is 1.00 pounds. As the 0.25 mL dose of infusible fluid 12 is two-and-a-half times the 0.10 mL increments in which occlusion detection process 18 is configured to populate storage array 52, occlusion detection process 18 may "normalize" this rate-of-change force reading. Specifically, occlusion detection process 18 may divide 1.00 pounds by 0.25 mL to determine that the force changed 0.40 pounds per 0.10 mL. Accordingly, occlusion detection process 18 may calculate a rate-of-change force reading of 0.40 pounds for the first 0.10 mL dose of infusible fluid 12, 0.40 pounds for the second 0.10 mL dose of infusible fluid 12, and 0.20 pounds for the last 0.05 mL dose of infusible fluid 12.

Accordingly, occlusion detection process 18 may populate storage array 52 so that a first storage cell (associated with the first 0.10 mL dose of infusible fluid 12) defines an initial force reading of 0.00 pounds, a final force reading of 0.40 pounds and a rate-of-change force reading of 0.40 pounds. Further, occlusion detection process 18 may populate storage array 52 so that a second storage cell (associated with the first 0.10 mL dose of infusible fluid 12) defines an additional force reading of 0.40 pounds, a final force reading of 0.80 pounds and a rate-of-change force reading of 0.40 pounds.

Concerning the remaining 0.05 mL of the 0.25 mL dose of infusible fluid 12, as this is less than the 0.10 mL increment at which occlusion detection process 18 is configured to populate storage array 52, the next cell within storage array 52 will not be populated until an additional 0.05 mL dose of infusible fluid 12 is dispensed.

Continuing with the above-stated example, assume for illustrative purposes that infusion pump assembly 10 administers a 0.15 mL dose of infusible fluid 12. Occlusion detection process 18 may combine the first 0.05 mL of the 0.15 mL dose of infusible fluid 12 with the remaining 0.05 mL of the 0.25 mL dose of infusible fluid 12 to form a complete 0.10 mL increment for recording within storage array 52.

Again, occlusion detection process 18 may "normalize" the 0.15 mL dose of infusible fluid 12. Assume for illustrative purposes that when dispensing the 0.15 mL of infusible fluid 12, occlusion detection process 18 determines an initial force reading of 1.00 pounds and a final force reading of 1.60 pounds. In the manner described above, occlusion detection process 18 may divide 0.60 pounds (i.e., 1.60 pounds minus 1.00 pounds) by 0.15 mL to determine that the force changed 0.40 pounds per 0.10 mL. Accordingly, occlusion detection process 18 may calculate a rate-of-change force reading of 0.20 pounds for the first 0.05 mL of the 0.15 mL dose of infusible fluid 12, and 0.40 pounds for the remaining 0.10 mL of the 0.15 mL dose of infusible fluid 12.

Accordingly, occlusion detection process 18 may populate storage array 52 so that a third storage cell (associated with the combination of the first 0.05 mL of the 0.15 mL dose of infusible fluid 12 with the remaining 0.05 mL of the 0.25 mL dose of infusible fluid 12) defines an initial force reading of 0.80 pounds (i.e., which is the final force reading after the second 0.10 mL of the 0.25 mL dose of infusible fluid 12), a final force reading of 1.20 pounds (i.e., the sum of the initial force reading of 1.00 pounds plus the 0.20 pound offset for the first 0.05 mL of the 0.15 mL dose of infusible fluid 12) and a rate-of-change force reading of 0.40 pounds. Further, occlusion detection process 18 may populate storage array 52 so that a fourth storage cell (associated with the last 0.10 mL of the 0.15 mL dose of infusible fluid 12) defines an initial force reading of 1.20 pounds, a final force reading of 1.60 pounds and a rate-of-change force reading of 0.40 pounds.

In addition to comparing 118 the average rate-of-change force reading (e.g., AFR) to a threshold rate-of-change force reading to determine if the average rate-of-change force reading (e.g., AFR) exceeds the threshold rate-of-change force reading, occlusion detection process 18 may compare 126 one or more of the initial force reading and the final force reading to a threshold force reading to determine if either the initial force reading or the final force reading exceeds the threshold force reading. If either of the initial force reading or the final force reading exceeds the threshold force reading, an alarm sequence may be initiated 128 on infusion pump assembly 10.

For example, occlusion detection process 18 may define a threshold force reading, which if exceeded by either the initial force reading (which is determined prior to dispensing a dose of infusible fluid 12) or the final force reading (which is determined after dispensing a dose of infusible fluid 12), an occlusion is deemed to be occurring. Example of such a threshold force reading is 4.00 pounds. Therefore, if after dispensing a dose of infusible fluid 12, occlusion detection process 18 determines a final force reading of 5.20 pounds, occlusion detection process 18 may initiate 128 an alarm sequence, as 5.20 pounds exceeds the 4.00 threshold force reading. The alarm sequence initiated 128 may include any combination of visual-based (via display system 24), audible-based (via a speaker assembly, not shown), and vibration-based alarms (via a vibration assembly, not shown).

As discussed above, infusion pump assembly 10 may include battery assembly 32 configured to power infusion pump assembly 10. Before and/or after dispensing a dose of infusible fluid 12, occlusion detection process 18 may compare 130 the actual voltage level of battery assembly 32 to a minimum voltage requirement to determine if the actual voltage level of battery assembly 32 meets the minimum voltage requirement. If the actual voltage level does not meet the minimum voltage requirement, occlusion detection process 18 may initiate 132 an alarm sequence on infusion pump assembly 10. The alarm sequence initiated 132 may include any combination of visual-based (via display system 24), audible-based (via a speaker assembly, not shown), and vibration-based alarms (via a vibration assembly, not shown). For example, assume for illustrative purposes that battery assembly 32 is a 5.00 VDC battery assembly. Further, assume that the minimum voltage requirement is 3.75 VDC (i.e., 75% of normal voltage). Accordingly, if occlusion detection process 18 determines 130 that the actual voltage level of battery assembly 32 is 3.60 VDC, occlusion detection process 18 may initiate 132 an alarm sequence on infusion pump assembly 10.

Additionally, occlusion detection process 18 may monitor one or more of the displaceable mechanical components included within infusion pump assembly 10 to determine 134 if one or more displaceable mechanical components included within infusion pump assembly 10 were displaced an expected displacement in response to delivering a dose of infusible fluid 12. If the displaceable mechanical components monitored were not displaced the expected displacement in response to delivering a dose of infusible fluid 12, occlusion detection process 18 may initiate 136 an alarm sequence on infusion pump assembly 10. The alarm sequence initiated 134 may include any combination of visual-based (via display system 24), audible-based (via a speaker assembly, not shown), and vibration-based alarms (via a vibration assembly, not shown).

For example, upon processing logic 16 energizing motor assembly 26 to dispense 0.10 mL of infusible fluid 12, occlusion detection process 18 may (via displacement detection device 30) confirm that partial nut assembly 40 did indeed move the expected displacement. Accordingly, in the event that partial nut assembly 40 does not move the expected displacement, a mechanical failure (e.g. the failure of partial nut assembly 40, the failure of lead screw assembly 42, the failure of motor assembly 26) may have occurred. In the event that the expected displacement of partial nut assembly 40 cannot be confirmed, occlusion detection process 18 may initiate 136 alarm sequence on infusion pump assembly 10.

When determining whether partial nut assembly 40 was displaced the expected amount, tolerances may be utilized. For example. assume that to deliver a 0.10 mL dose of infusible fluid 12, occlusion detection process 18 may expect to see partial nut assembly 40 displaced 0.050 inches. Accordingly, occlusion detection process 10 may utilize a 10% error window in which movement of partial nut assembly 40 of less than 0.045 inches (i.e., 10% less than expected) would result in occlusion detection process 18 initiating 136 alarm sequence on infusion pump assembly 10.

In one embodiment of displacement detection device 30, displacement detection device 30 includes one or more light sources (not shown) positioned on one side of partial nut assembly 40 and one or more light detectors (not shown) positioned on the other side of partial nut assembly 40. Partial nut assembly 40 may include one or more passages (not shown) through which the light from the one or more light sources (not shown) included within displacement detection device 30 may shine and may be detected by the one or more light detectors (not shown) included within displacement detection device 30.

A number of implementations have been described. Nevertheless, it will be understood that various modifications may be made. Accordingly, other implementations are within the scope of the following claims.

What is claimed is:

1. A method for an infusion pump assembly, wherein the infusion pump assembly comprises a reservoir assembly and a pump assembly, the pump assembly including a plunger assembly and a motor assembly, the method comprising:
- storing an infusible fluid in the reservoir assembly;
- displacing the plunger assembly that is operably connected to the reservoir assembly in response to signals received by the motor assembly from a processing logic;
- dispensing the infusible fluid from the reservoir assembly through a cannula assembly
- monitoring one or more displaceable mechanical components included within the infusion pump assembly to determine if the one or more displaceable mechanical components were displaced an expected displacement in response to delivery of one or more of the first dose of the infusible fluid and the second dose of the infusible fluid; and
- if the one or more displaceable mechanical components were not displaced the expected displacement in response to delivery of one or more of the first dose of the infusible fluid and the second dose of the infusible fluid, initiating an alarm sequence on the infusion pump assembly.

2. The method of claim 1, wherein the infusion pump assembly includes a processing logic which includes at least one microprocessor configured to interact with a memory system, the method further comprising:
- storing instruction sets and subroutines of an occlusion detection process on the memory system; and
- accessing and executing said instruction sets and subroutines via the connection between the processing logic and the at least one microprocessor.

3. The method of claim 1, wherein the infusion pump assembly includes a battery assembly configured to power the infusion pump assembly, the method further comprising:
- comparing an actual voltage level of the battery assembly to a minimum voltage requirement to determine if the actual voltage level meets the minimum voltage requirement;
- if the actual voltage level does not meet the minimum voltage requirement, initiating an alarm sequence on the infusion pump assembly, wherein the alarm sequence includes any combination of visual-based, audible-based and/or vibration-based alarms.

4. The method of claim 1, further comprising:
- determining a first initial reading prior to dispensing a first dose of an infusible fluid;
- dispensing the first dose of the infusible fluid;
- monitoring a volume of the infusible fluid dispensed in the first dose;
- determining a second initial reading prior to dispensing a second dose of the infusible fluid;
- setting a first final reading value as being equal to the second initial reading;
- dispensing the second dose of the infusible fluid;
- monitoring a volume of the infusible fluid dispensed in the second dose;
- determining a second final reading subsequent to dispensing the second dose of the infusible fluid;
- determining a first rate-of-change reading that corresponds to the delivery of the first dose of the infusible fluid via an infusion pump assembly by subtracting the first initial reading from the first final reading value;
- determining at least a second rate-of-change reading that corresponds to the delivery of the second dose of the infusible fluid via the infusion pump assembly by subtracting the second initial reading from the second final reading;
- normalizing the first rate-of-change reading and the second rate-of-change reading to be indicative of the rates-of-change sensed for an equivalent quantity of infusible fluid; and
- determining an average rate-of-change reading based, at least in part upon the normalized first rate-of-change reading and the normalized at least a second rate-of-change reading.

5. The method of claim 1, further comprising:
- comparing the average rate-of-change reading to a threshold rate-of-change reading to determine if the average rate-of-change reading exceeds the threshold rate-of-change reading; and
- if the average rate-of-change reading exceeds the threshold rate-of-change reading, initiating an alarm sequence on the infusion pump assembly.

6. The method of claim 1, further comprising:
- comparing one or more of the first initial reading and the first final reading to a threshold reading to determine if one or more of the first initial reading and the first final reading exceeds the threshold reading; and
- if one or more of the first initial reading and the first final reading exceeds the threshold reading, initiating an alarm sequence on the infusion pump assembly.

7. The method of claim 1, wherein the infusion pump assembly includes a battery assembly configured to power the infusion pump assembly, the method further comprising:

comparing an actual voltage level of the battery assembly to a minimum voltage requirement to determine if the actual voltage level meets the minimum voltage requirement; and if the actual voltage level does not meet the minimum voltage requirement, initiating an alarm sequence on the infusion pump assembly.

8. A computer program product residing on a non-transitory computer readable medium in an infusion pump assembly having a plurality of instructions stored thereon which, when executed by a processing logic, cause the processing logic to perform operations comprising:

storing an infusible fluid in a reservoir assembly;

displacing a plunger assembly that is operably connected to the reservoir assembly in response to signals received by a motor assembly from the processing logic;

dispensing the infusible fluid from the reservoir assembly through a cannula assembly determining a first initial reading prior to dispensing a first dose of an infusible fluid;

dispensing the first dose of the infusible fluid;

monitoring a volume of the infusible fluid dispensed in the first dose;

determining a second initial reading prior to dispensing a second dose of the infusible fluid;

setting a first final reading value as being equal to the second initial reading;

dispensing the second dose of the infusible fluid;

monitoring a volume of the infusible fluid dispensed in the second dose;

determining a second final reading subsequent to dispensing the second dose of the infusible fluid;

determining a first rate-of-change reading that corresponds to the delivery of the first dose of the infusible fluid via an infusion pump assembly by subtracting the first initial reading from the first final reading value;

determining at least a second rate-of-change reading that corresponds to the delivery of the second dose of the infusible fluid via the infusion pump assembly by subtracting the second initial reading from the second final reading;

normalizing the first rate-of-change reading and the second rate-of-change reading to be indicative of the rates-of-change sensed for an equivalent quantity of infusible fluid; and determining an average rate-of-change reading based, at least in part upon the normalized first rate-of-change reading and the normalized at least a second rate-of-change reading.

9. The computer program product of claim 8, further comprising instructions for:

comparing the average rate-of-change reading to a threshold rate-of-change reading to determine if the average rate-of-change reading exceeds the threshold rate-of-change reading; and if the average rate-of-change reading exceeds the threshold rate-of-change reading, initiating an alarm sequence on the infusion pump assembly.

10. The computer program product of claim 8, further comprising instructions for:

comparing one or more of the first initial reading and the first final reading to a threshold reading to determine if one or more of the first initial reading and the first final reading exceeds the threshold reading; and if one or more of the first initial reading and the first final reading exceeds the threshold reading, initiating an alarm sequence on the infusion pump assembly.

11. The computer program product of claim 8, wherein the infusion pump assembly includes a battery assembly configured to power the infusion pump assembly, the computer program product further comprising instructions for:

comparing an actual voltage level of the battery assembly to a minimum voltage requirement to determine if the actual voltage level meets the minimum voltage requirement; and if the actual voltage level does not meet the minimum voltage requirement, initiating an alarm sequence on the infusion pump assembly.

12. An infusion pump assembly configured to perform operations comprising:

storing an infusible fluid in a reservoir assembly;

displacing a plunger assembly that is operably connected to the reservoir assembly in response to signals received by a motor assembly from a processing logic;

dispensing the infusible fluid from the reservoir assembly through a cannula assembly determining a first initial reading prior to dispensing a first dose of an infusible fluid;

dispensing the first dose of the infusible fluid;

monitoring a volume of the infusible fluid dispensed in the first dose;

determining a second initial reading prior to dispensing a second dose of the infusible fluid;

setting a first final reading value as being equal to the second initial reading;

dispensing the second dose of the infusible fluid;

monitoring a volume of the infusible fluid dispensed in the second dose;

determining a second final reading subsequent to dispensing the second dose of the infusible fluid;

determining a first rate-of-change reading that corresponds to the delivery of the first dose of the infusible fluid via an infusion pump assembly by subtracting the first initial reading from the first final reading value;

determining at least a second rate-of-change reading that corresponds to the delivery of the second dose of the infusible fluid via the infusion pump assembly by subtracting the second initial reading from the second final reading;

normalizing the first rate-of-change reading and the second rate-of-change reading to be indicative of the rates-of-change sensed for an equivalent quantity of infusible fluid; and determining an average rate-of-change reading based, at least in part upon the normalized first rate-of-change reading and the normalized at least a second rate-of-change reading.

13. The infusion pump assembly of claim 12, wherein the infusion pump assembly is further configured to perform operations comprising:

comparing the average rate-of-change reading to a threshold rate-of-change reading to determine if the average rate-of-change reading exceeds the threshold rate-of-change reading; and if the average rate-of-change reading exceeds the threshold rate-of-change reading, initiating an alarm sequence on the infusion pump assembly.

14. The infusion pump assembly of claim 12, wherein the infusion pump assembly is further configured to perform operations comprising:

comparing one or more of the first initial reading and the first final reading to a threshold reading to determine if one or more of the first initial reading and the first final reading exceeds the threshold reading; and if one or more of the first initial reading and the first final reading exceeds the threshold reading, initiating an alarm sequence on the infusion pump assembly.

15. The infusion pump assembly of claim 12, wherein the infusion pump assembly includes a battery assembly configured to power the infusion pump assembly and the infusion pump assembly is further configured to perform operations comprising:

comparing an actual voltage level of the battery assembly to a minimum voltage requirement to determine if the actual voltage level meets the minimum voltage requirement; and if the actual voltage level does not meet the minimum voltage requirement, initiating an alarm sequence on the infusion pump assembly.

* * * * *